(12) United States Patent
Fleming, III

(10) Patent No.: US 6,312,394 B1
(45) Date of Patent: Nov. 6, 2001

(54) BONE MARROW BIOPSY DEVICE

(75) Inventor: James A. Fleming, III, Buffalo Grove, IL (US)

(73) Assignee: Manan Medical Products, Inc., Wheeling, IL (US)

(*) Notice: Subject to any disclaimer, the term of this patent is extended or adjusted under 35 U.S.C. 154(b) by 0 days.

(21) Appl. No.: 09/677,819

(22) Filed: Sep. 29, 2000

Related U.S. Application Data

(63) Continuation-in-part of application No. 09/557,815, filed on Apr. 25, 2000.

(51) Int. Cl.[7] .................................................. A61B 5/00
(52) U.S. Cl. ........................................................ 600/567
(58) Field of Search .......................... 600/562, 564–567; 606/167, 170

(56) References Cited

U.S. PATENT DOCUMENTS

| | | | |
|---|---|---|---|
| D. 303,009 | 8/1989 | Strasser et al. | D24/24 |
| 3,844,291 | 10/1974 | Moen | 128/354 |
| 4,403,617 | 9/1983 | Tretinyak | 128/754 |
| 4,630,616 | 12/1986 | Tretinyak | 128/753 |
| 4,651,752 | 3/1987 | Fuerst | 128/754 |
| 4,655,226 | 4/1987 | Lee | 128/754 |
| 4,785,826 | 11/1988 | Ward | 128/754 |
| 4,838,282 | 6/1989 | Strasser et al. | 128/754 |
| 5,074,311 | 12/1991 | Hasson | 128/754 |
| 5,148,813 | 9/1992 | Bucalo | 128/754 |
| 5,172,700 | 12/1992 | Becini et al. | 128/751 |
| 5,286,255 | 2/1994 | Weber | 604/22 |
| 5,318,589 | 6/1994 | Lichtman | 606/205 |
| 5,333,619 | 8/1994 | Burgio | 128/754 |
| 5,357,974 | 10/1994 | Baldridge | 128/754 |
| 5,462,062 | 10/1995 | Rubinstein et al. | 128/754 |
| 5,522,398 | 6/1996 | Goldenberg et al. | 128/754 |
| 5,595,186 | 1/1997 | Rubenstein et al. | 128/754 |
| 5,634,473 | 6/1997 | Goldenberg et al. | 128/754 |

*Primary Examiner*—Max Hindenburg
(74) *Attorney, Agent, or Firm*—Dick and Harris

(57) ABSTRACT

The present invention is directed to a bone marrow biopsy device including an outer cannula, an outer cannula handle having a locking member, an inner rod, an inner rod handle having a locking member, and an independent locking element. The outer cannula handle locking member further comprises a flange element, and the inner rod handle locking member further comprises at least one prong. In one embodiment, the locking element comprises a cylindrical sleeve surrounding the at least one prong and the flange element. The cylindrical sleeve comprises at least one slot which aligns with the at least one prong when the locking element is in its unlocked orientation. The locking element is placed into its locked orientation by rotation of the locking element about the at least one prong and the flange element such that the at least one prong no longer aligns with the at least one slot and is therefore prevented from passing over the flange element. In another embodiment, the locking element comprises at least one bar extending completely through the inner rod handle, preventing disengagement of the at least one prong from the at least one flange element. Further, the bone marrow biopsy device may include at least one grip enhancement member formed from a material distinct from that of the handles, which may extend outwardly such that the user's palm is prevented from coming in contact with the locking element during use of the device.

22 Claims, 6 Drawing Sheets

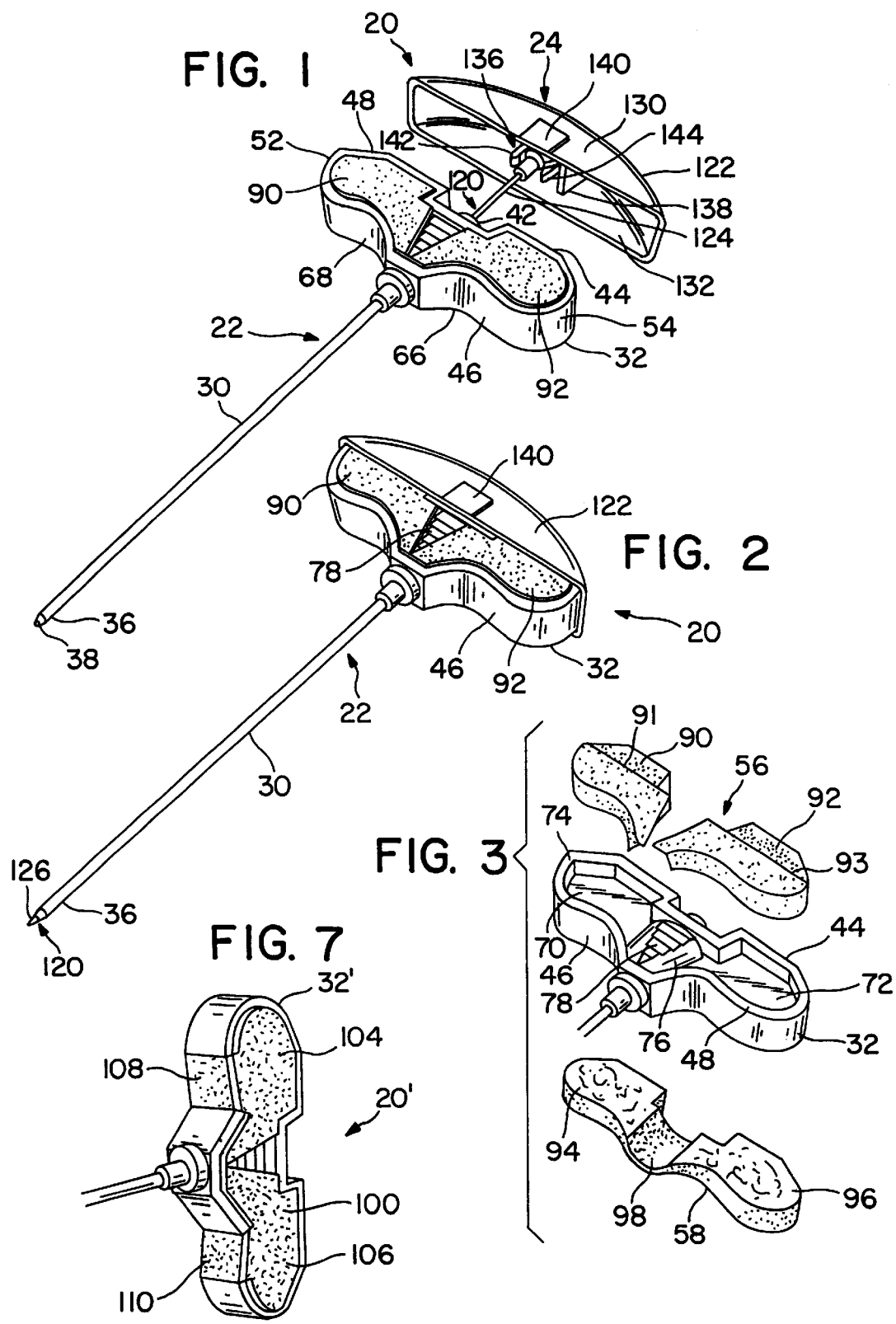

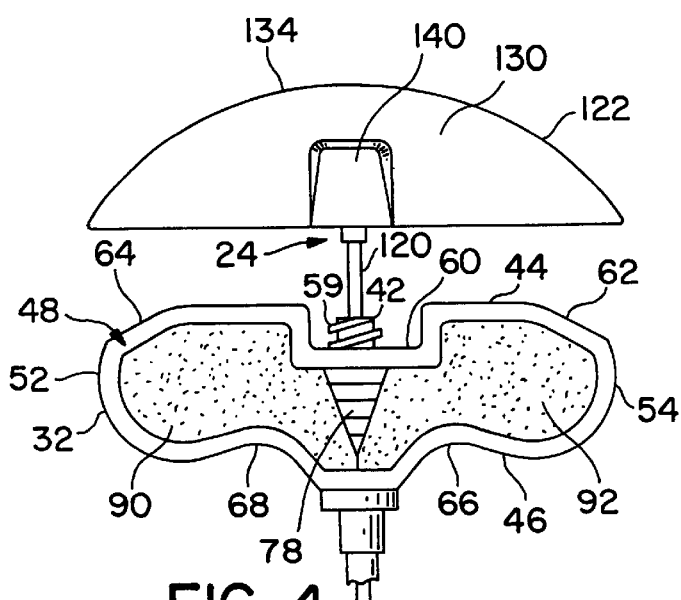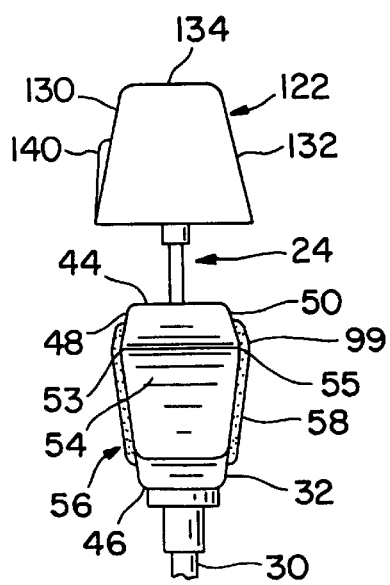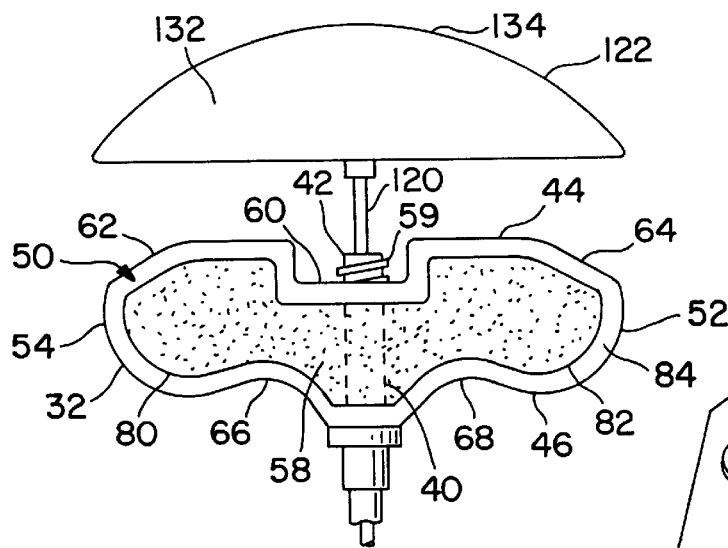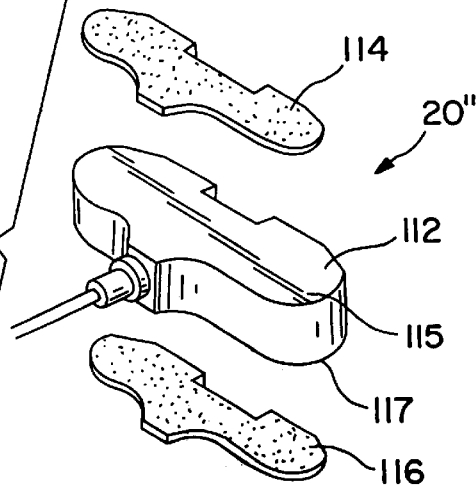

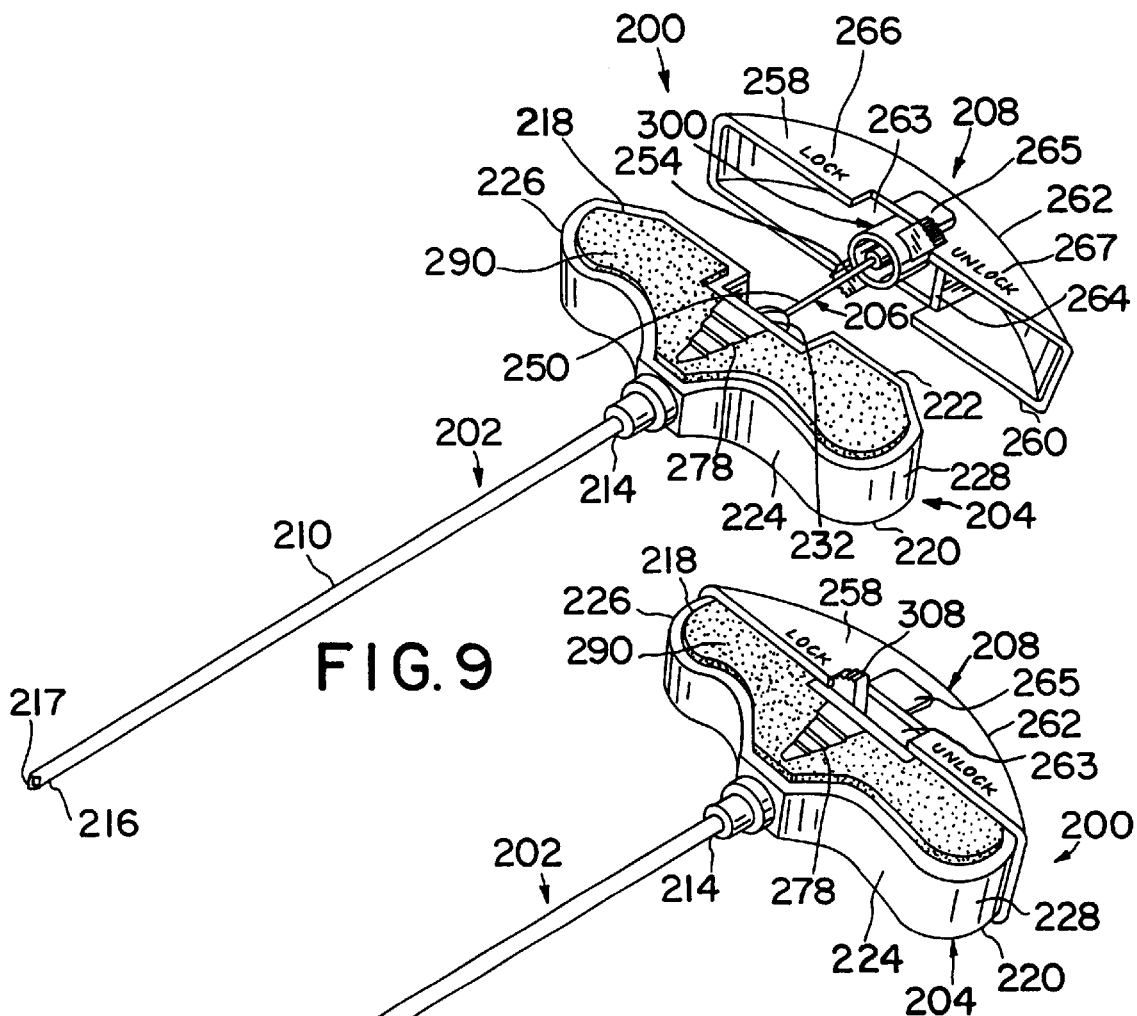
FIG. 9
FIG. 10
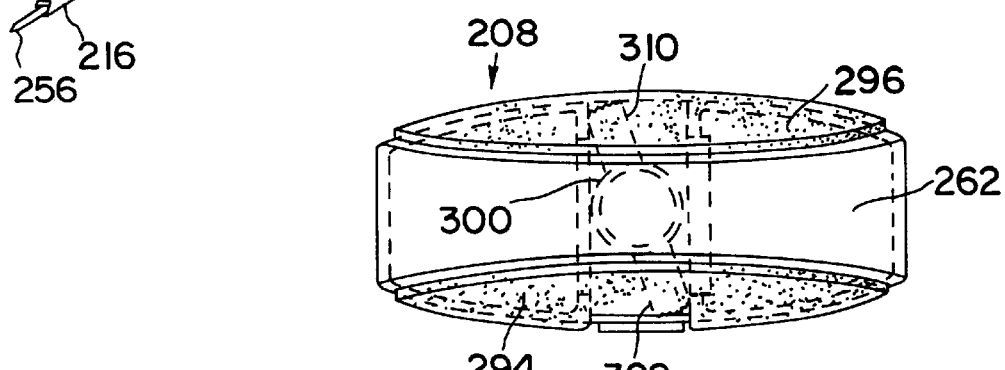
FIG. 19

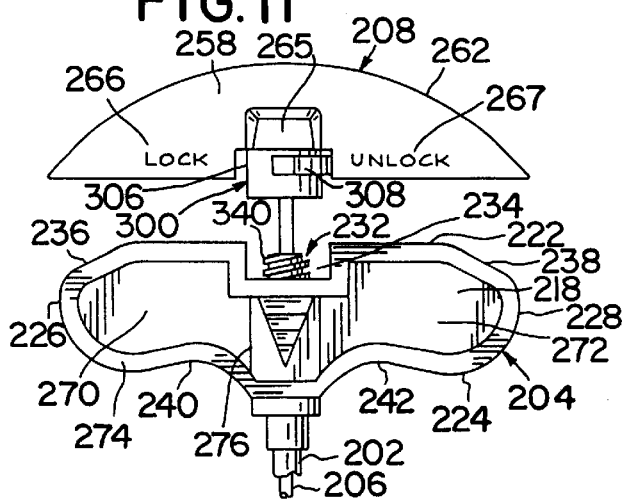
FIG. 11
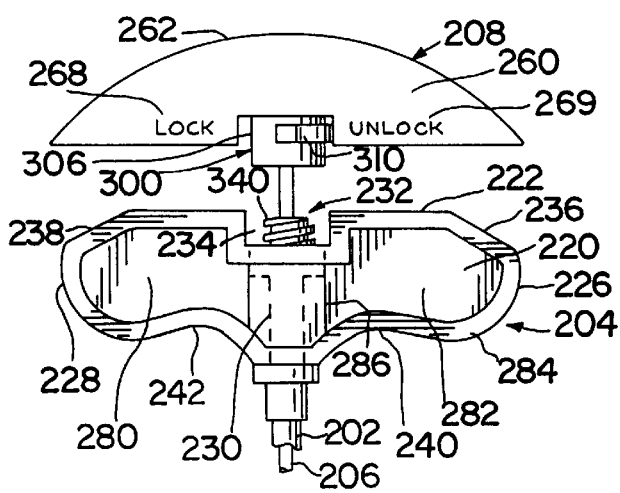
FIG. 12
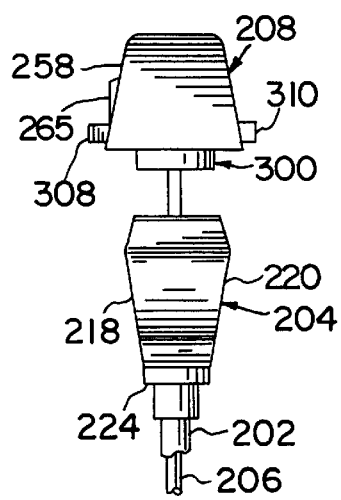
FIG. 13
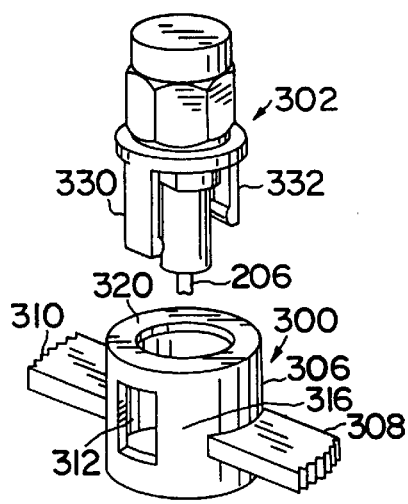
FIG. 14
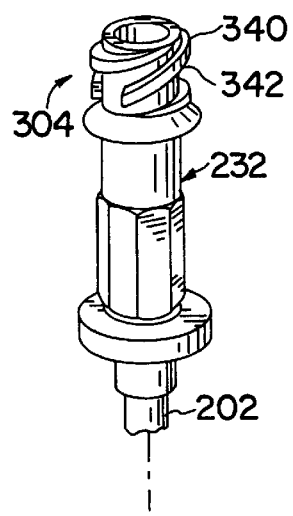

BONE MARROW BIOPSY DEVICE

The present application is a continuation-in-part application of Ser. No. 09/557,815, filed Apr. 25, 2000.

BACKGROUND OF THE INVENTION

1. Field of the Invention

The present invention relates in general to bone marrow biopsy devices and, more particularly, to a bone marrow biopsy device with a grip enhancement feature and a securable locking mechanism.

2. Background Art

Bone marrow biopsy devices have been known in the art for many years. In particular, many bone marrow biopsy devices have included a hollow outer cannula with some form of inner rod slidable within the outer cannula. The outer cannula conventionally consists of a proximal end, a distal end and some form of a handle associated with the proximal end. The inner rod may typically take several different forms, including a sharpened stylet for insertion of the bone marrow biopsy needle into a patient, an inner cannula for sampling bone marrow, and/or an ejector rod for forcing the sample out of the outer cannula. The inner rod also typically includes a second or connection handle which may be secured to the handle portion of the outer cannula.

For instance, Baldridge, U.S. Pat. No. 5,357,974, Tretinyak, U.S. Pat. No. 4,403,617, Tretinyak, U.S. Pat. No. 4,630,616, Lee, U.S. Pat. No. 4,655,266 and Strasser et al., U.S. Pat. No. 4,838,282 all disclose bone marrow biopsy devices having a first handle mounted on the outer cannula and a second handle mounted on the inner rod. The first and second handle portions of these devices are constructed from the same material, typically a light weight plastic. Moreover, these handles are usually designed to securably mate with one another, for instance by a locking member, such as that taught in Mittermeier et al., U.S. Pat. No. 6,063,037, incorporated herein by reference.

Additionally, several of these bone marrow biopsy devices have included handle features which enhance the ability of a user to both grip and manipulate the bone marrow biopsy needle. For instance, Strasser, U.S. Pat. No. 4,838,282 discloses finger grooves in the outer cannula handle portion, while Tretinyak, U.S. Pat. No. 4,403,617 discloses ridges on both the first and second handle portions to facilitate a user's grasping of the device.

Although these and other bone marrow biopsy devices have worked well, it is still desired to provide an enhanced gripping surface which enhances the feel for a user of the instrument, while at the same time preventing slipping of a hand or fingers which grasp the handle portion of the instrument. It is likewise desired to provide an enhanced gripping surface which works well in condition where water, perspiration or other fluid may be present.

It is further desired to provide a bone marrow biopsy device with a handle having a cushioned gripping portion. In particular, many bone marrow biopsy devices must inherently be forced by a physician for insertion into a patient's bone, thus mandating a firm, tight grip on the handle of the instrument. It is beneficial to provide a softer, cushioned surface to alleviate some of the stress placed on the physician's hand.

It is also desirable to provide a bone marrow biopsy device with a handle which is easily molded, and which includes inserts which add to the weight of the handle and improve weight distribution throughout the handle. It is likewise desirable to provide an inexpensive, easily positioned insert which contributes to a comfortable handle weight, while also enhancing the grip of the handle.

It is also desired to provide a bone marrow biopsy device with a gripping surface which enhances the secured, locking relationship of the outer cannula handle portion to the inner rod handle portion, to facilitate simultaneous use of the outer cannula in conjunction with the inner rod, for insertion, manipulation, and removal of the bone marrow biopsy device from a patient.

With regard to yet other device features, numerous bone marrow biopsy devices in the prior art have provided a secure, locked engagement between the cannula and rod handle segments. Many of these have required rotation of one of the handles themselves to return them to an unlocked orientation, resulting in a change in the orientation of the handles with respect to one another. This change in orientation of the handles, however, also causes a corresponding change in the orientation of the inner rod with respect to the outer cannula, which can be undesirable to the user. Likewise, the manipulations of the overall device while in use can inadvertently separate the cannula handle from the rod handle, unlocking the device and causing the aligned tips of the cannula and rod to become misaligned. For many applications, the user will want to remove the inner rod while the bone marrow biopsy device is inserted into a patient, and undesired rotation of the inner rod during removal may jeopardize the patient or the sample which the user wishes to remove. These bone marrow biopsy devices also present an increased risk of accidental separation of the handles during insertion of the device into the patient, due to unintended rotation of the handles with respect to one another caused by the twisting force exerted on the handle by the user as he attempts to force the device through the patient's bone and tissue.

In yet other lockable biopsy devices, a locknut securing device positioned directly atop the inner rod must be repeatedly rotated for removal, thereby allowing the user to directly remove the rod itself from the interior of the cannula. These devices typically do not include a handle at all for the rod and are often difficult to use, particularly with regard to the handling of the rod after it has been removed from the cannula.

As a result, it is desired to provide a bone marrow biopsy device with separate handle segments for both the cannula and rod elements, having an independent locking element which provides a secure, locked engagement between the two handles and yet allows the user to lock and unlock the handles without having to affect the orientation of the handles with respect to one another. It is further desired to allow the user of the bone marrow biopsy device to readily unlock and separate the handles, in order to remove the inner rod, without affecting their orientation, in order to prevent an undesired corresponding change in orientation of the inner rod distal end with respect to the outer cannula distal end.

It is also desired to provide a bone marrow biopsy device with a gripping surface which lessens the risk of accidental unlocking and separation of the handles—by preventing the palm of the user's hand from coming into inadvertent contact with the locking element.

These and other objects of the present invention will become apparent in light of the present specification, claims and drawings.

SUMMARY OF THE INVENTION

The present invention is directed to a bone marrow biopsy needle including an outer cannula and an inner rod. The outer cannula includes a proximal end, a distal end, a hollow section therebetween and a handle portion associated with the proximal end. The handle portion further includes a front portion, a rear portion, a top portion, a bottom portion and a grip enhancement member which is formed from a material distinct from at least a portion of the handle portion.

In a preferred embodiment, the grip enhancement member comprises at least one tactile insert member. The at least one tactile insert member preferably fits into at least one corresponding cavity in the handle portion of the outer cannula. In one embodiment, handle portion includes cavities in both the front and rear portions, both of which contain separate front and rear tactile insert members. In another embodiment, the front portion includes two separate cavities, each of which include separate tactile inserts.

In a preferred embodiment, the at least one tactile insert member is constructed from rubber. The rubber provides a non-slip gripping surface, while enhancing gripping ability under wet conditions, such as those generated by a perspiring palm or other liquids in the surgical environment. The grip enhancement member also provides cushioning for a user and adds weight to the handle portion to facilitate weight distribution throughout the outer cannula handle.

In another preferred embodiment, the at least one insert member is constructed from other, preferably heavier materials, to add additional weight to the handle portion of the outer cannula.

In one embodiment, the grip enhancement member comprises a single piece extending from a front portion cavity, across at least a portion of the bottom portion, and into a back portion cavity. In another embodiment, the grip enhancement member comprises a tactile overlay attached to one or both of the front and rear portions of the handle portion of the outer cannula.

The inner rod includes a proximal end, a distal end and a handle cap. The inner rod may take the form of a sharpened stylet, an inner cannula, an ejector rod, or other solid or hollow rods. The handle cap is preferably associated with the proximal end of the inner rod, and is capable of securable engagement with the handle portion of the outer cannula to facilitate simultaneous insertion of the outer cannula and the inner rod into and removal from a patient.

In a preferred embodiment, the grip enhancement member extends outwardly beyond the handle portion to enhance the secured engagement of the outer cannula with the inner rod when the handle cap is positioned over the handle portion of the outer cannula in a locking orientation.

In another preferred embodiment, the handle cap includes a separate locking member for releasably locking the handle cap onto the handle portion of the outer cannula. In yet another preferred embodiment, the handle cap includes an alignment member for alignment with an orientation indicia on the handle portion of the outer cannula for directing proper orientation of the handle cap onto the handle portion.

In yet another embodiment, the present invention is directed to a bone marrow biopsy needle including an outer cannula, an inner rod, an outer cannula handle, an inner rod handle, and a locking element. In this embodiment also, the outer cannula includes a proximal end, a distal end, and a hollow section therebetween. The outer cannula handle includes a locking member and is operably attached to the outer cannula at the proximal end of the outer cannula. The inner rod includes a proximal end and a distal end. The inner rod handle includes a locking member, is operably attached to the inner rod at the proximal end of the inner rod, and is capable of securable engagement with the outer cannula handle to facilitate simultaneous insertion of the outer cannula and the inner rod into and removal from a patient. The locking element is associated with locking members on both the outer cannula handle and the inner rod handle, and is capable of alternatively locking and releasing the handles—notably without having to reorient their positions relative to one another. In this embodiment, the inner rod itself may take the form of a sharpened stylet, an inner cannula, an ejector rod, or other solid or hollow rods.

In another embodiment, the outer cannula handle nests within the inner rod handle when the handles are joined together.

In yet another embodiment, the locking member associated with the outer cannula handle comprises at least one flange element located on the outer cannula handle.

Preferably, the locking member associated with the inner rod handle comprises at least one prong capable of engaging with the at least one flange element located on the outer cannula handle to prevent separation of the handles from one another.

In this embodiment, the locking element comprises a cylindrical sleeve surrounding the at least one prong and at least one flange element which prevents disengagement of the at least one prong from the at least one flange element.

In another embodiment, the at least one flange element further comprises at least a portion of the conventional thread found on typical threaded connectors for medical devices, that allow the user to attach the threaded component adjacent the outer cannula handle to other conduits, such as for suction, after removing the inner rod from the outer cannula.

In this embodiment also, the locking element includes at least one slot such that the at least one prong in the inner rod handle locking member is able to partially protrude through the at least one slot when the locking element is in an unlocked orientation.

In this embodiment the locking element may be rotated by the user, with respect to the at least one prong and the at least one flange element, in order to place the locking element in a locked orientation, wherein said at least one prong is prevented from partially protruding through said at least one slot by said locking element.

In the preferred embodiment, the locking element further includes at least one locking tab, which facilitates rotation of the locking element with respect to the at least one prong and the at least one flange element, thereby permitting locking and unlocking of the locking element without affecting the orientation of the handles themselves.

In another preferred embodiment, the bone marrow biopsy device further includes an alignment member associated with at least one of the outer cannula handle and the inner rod handle, which serves to ensure proper orientation of the handles with respect to one another when the handles are joined together by the user.

In this embodiment, at least one of the outer cannula handle and the inner rod handle includes an opening capable of receiving the alignment member and which may be positioned such that the handles can only be fully joined in the proper orientation when the alignment member is properly oriented with respect to the opening.

In this embodiment also, the bone marrow biopsy device further includes an alignment indicia for visually indicating proper orientation of the handles with respect to one another during engagement of the handles.

In yet another preferred embodiment, the bone marrow biopsy device further includes locking indicia for indicating whether the locking element is in its locked or unlocked orientation. Preferably, the locking indicia comprises text printed on at least one of the outer cannula handle and inner rod handle which corresponds to the position of the at least one locking tab—to indicate to the user whether the locking element is in its locked or unlocked orientation.

In yet another embodiment, at least one of the outer cannula handle and the inner rod handle further includes at least one grip enhancement member facilitating handling and use of the bone marrow biopsy device. In one embodiment, the at least one grip enhancement member is formed from a material distinct from the handles. In another embodiment, the at least one grip enhancement member is at least partially constructed from rubber or other elastomeric material.

Preferably, the at least one grip enhancement member extends outwardly beyond the end of the at least one locking tab of the locking element, thereby preventing the palm of the user from coming into casual contact with, and possibly engaging, the locking tabs during use of the bone marrow biopsy device.

In this embodiment also, the at least one grip enhancement member extends outwardly beyond at least a portion of the outer cannula handle to enhance the secured engagement of the outer cannula handle and inner rod handle by forming an interference fit between the handles.

In another embodiment of the invention, the locking element comprises at least one bar extending completely through the inner rod handle, which prevents disengagement of the prong from the flange element when the locking element is in its locked orientation. Preferably, the locking element further includes at least one finger tab to facilitate manipulation of the locking element by the user.

BRIEF DESCRIPTION OF THE DRAWINGS

FIG. 1 is an exploded perspective view of the bone marrow biopsy device according to the present invention;

FIG. 2 is a perspective view of the bone marrow biopsy device as shown in FIG. 1, with the handle cap in a locked orientation relative to the handle portion of the outer cannula;

FIG. 3 is a fragmentary exploded perspective view of the handle portion of the outer cannula of the bone marrow biopsy device shown in FIG. 1;

FIG. 4 is a front elevational view of a portion of the bone marrow biopsy device shown in FIG. 1;

FIG. 5 is a side elevational view of a portion of the bone marrow biopsy device shown in FIG. 1;

FIG. 6 is a rear elevational view of a portion of the bone marrow biopsy device shown in FIG. 1;

FIG. 7 is a perspective view of the handle portion of the bone marrow biopsy device according to another embodiment of the invention; and FIG. 8 is an exploded perspective view of the handle portion of the bone marrow biopsy device according to yet another embodiment of the present invention.

FIG. 9 is an exploded perspective view of the bone marrow biopsy device according to the present invention showing the outer cannula handle and inner rod handle prior to being joined;

FIG. 10 is a perspective view of the bone marrow biopsy device as shown in FIG. 9, with the outer cannula handle and inner rod handle joined together and the locking element in its locked orientation;

FIG. 11 is a front elevational view of a portion of the bone marrow biopsy device shown in FIG. 9 with the locking element in its unlocked orientation and a portion of the inner rod retracted from the outer cannula;

FIG. 12 is a rear elevational view of a portion of the bone marrow biopsy device shown in FIG. 9 with the locking element shown in its unlocked orientation and a portion of the inner rod retracted from the outer cannula;

FIG. 13 is a side elevational view of a portion of the bone marrow biopsy device shown in FIG. 9 with the locking element shown in its unlocked orientation and a portion of the inner rod retracted from the outer cannula;

FIG. 14 is an exploded perspective view of the locking element of the bone marrow biopsy device shown in FIG. 9 showing the inner rod handle locking member, the outer cannula handle locking member, and the locking element that cooperates with the two locking members to alternately lock and release the handles from one another;

FIG. 19 is a top plan view of the bone marrow biopsy device according to another embodiment of the invention, in which a grip enhancement member isolates the locking tab on the locking element, from inadvertent toggling by the palm of the user of the bone marrow biopsy device;

DETAILED DESCRIPTION OF THE INVENTION

Figure 15:
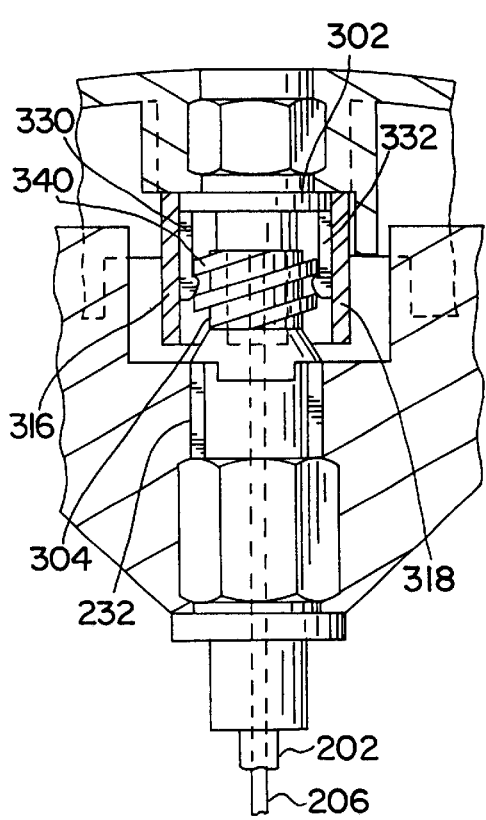
FIG. 15 is a cross-sectional view of the locking element of the bone marrow biopsy device shown in FIG. 9 in its locked orientation, showing the prongs of the inner rod handle locking member engaged with the flange element of the outer cannula handle locking member, as confined by the locking element sidewall.

While this invention is susceptible of embodiment in many different forms, there is shown in the drawings, and will herein be described in detail, several specific embodiments, with the understanding that the present disclosure can be considered as an exemplification of the principals of the invention and is not intended to limit the invention to the embodiments illustrated.

Bone marrow biopsy device 20 is shown in FIGS. 1–6 as comprising outer cannula 22 and inner rod 24. At the outset, while the present invention will be described in the specific context of a bone marrow biopsy device, the invention is certainly not limited to just bone marrow biopsy instruments. Indeed, the present invention may be used in conjunction with a multitude of medical or other instruments. Likewise, the present invention is effective for use in not only bone marrow biopsy retrieval procedures, but also with other instruments to perform other tissue retrieval procedures, other procedures involving the aspiration and/or injection of fluids or other materials through a instrument handle, or even other procedures and associated instruments as would be known by those of ordinary skill in the art with the present disclosure before them. Throughout this detailed description, like reference numerals will be used to designate like parts.

Also at the outset, while inner rod 24 is shown in the drawings as comprising a sharpened stylet or obturator used for cutting through soft and hard bone tissue, inner rod 24 may likewise comprise a hollow inner cannula used for sampling bone marrow tissue, an ejector rod for forcing that tissue from that outer cannula, as well as other types of inner rods well known by those of ordinary skill in the art with the present disclosure before them. Certain inner rod structures are disclosed in Mittermeier, U.S. Pat. No. 6,063,037, incorporated herein by reference.

Outer cannula 22, shown in FIGS. 1–6, includes cylindrical tube portion 30 and handle portion 32. Cylindrical tube portion 30 includes both proximal end 34 and distal end 36. Distal end 36 is shown in FIGS. 1 and 2 as having saddle point configuration 38 with sharp edges. Such a configuration, as is well known in the art, facilitates cutting through both soft and hard tissue, thus facilitating the entry of the bone marrow biopsy device into a bone marrow sampling region. However, it is likewise contemplated that other distal end point configurations may likewise be utilized with the present invention, depending on the specific biopsy application. Moreover, distal end 36 of cylindrical tube portion 30 may likewise include an inner tapered portion to facilitate bone marrow retrieval, such as disclosed in Mittermeier, U.S. Pat. No. 6,063,037.

Handle portion 32 is shown in FIGS. 1–6 as including aperture 40, connecting tube 42, top portion 44, bottom portion 46, front portion 48, rear portion 50, first side portion 52, second side portion 54, front tactile insert member 56 and rear tactile insert member 58. Aperture 40 connects cylindrical tube portion 30 with connecting tube 42, which includes ridge 59 to facilitate locking of inner rod 24 to outer cannula 22, as will be described in more detail below. Ridge 59 may comprise a threaded region, such as that shown in FIGS. 4 and 6, or any other contoured portion which facilitates receipt of inner rod 24.

Top portion 44 includes notch 60 and sloping portions 62 and 64. Notch 60, best seen in FIGS. 4 and 6, permits connecting tube 42 to exit aperture 40 of handle portion 32. As can be seen from the drawings, notch 60 is preferably off-center relative to connecting tube 42, so as to provide a larger space on one side of the connecting tube. Sloping portion 62 and 64 preferably extend from top portion 44 down to side portions 52 and 54, and facilitate a contoured fit of handle cap 122 onto handle portion 32.

Bottom portion 46 preferably includes finger grooves 66 and 68. The finger grooves facilitate grasping of handle portion 32 by a physician. However, while finger grooves 66 and 68 are certainly preferred, handle portion 32 may likewise be rounded or squared on bottom portion 46 without any finger grooves or special receptacles for a user's fingers.

Front portion 48, shown in FIGS. 1–5, includes first cavity 70, second cavity 72, outer peripheral ridge 74 and barrel portion 76. First cavity 70 and second cavity 72, as can be seen in FIG. 3, are positioned on either side of barrel portion 76, which further includes orientation indicia 78. As can be seen in the drawings, orientation indicia 78 helps a user distinguish between the front and rear sides of bone marrow biopsy device 20, so as to properly indicate the orientation of distal end 36 of outer cannula 22 and/or the orientation of inner rod 24, for instance in those applications where the inner rod comprises a sharpened stylet. Moreover, while orientation indicia 78 is shown in the drawings as comprising a stepped arrow, any orientation indicia may be used in conjunction with the present invention as would be known by those with ordinary skill in the art with the present disclosure before them. Outer peripheral ridge 74 forms a wall around first cavity 70 and second cavity 72.

Rear portion 50, shown in FIGS. 3, 5 and 6, likewise includes first cavity 80, second cavity 82, outer peripheral ridge 84 and a barrel portion (not shown, but preferably similar to barrel portion 76 on front portion 48, without an orientation indicia). Like first 70 and second 72 cavities in front portion 48, first cavity 80 and second cavity 82 are separated by the barrel portion, and enclosed by outer peripheral ridge 84.

Front tactile insert member 56 is shown in FIGS. 1–5 as including first front insert 90 and second front insert 92. Front tactile insert member 56 preferably comprises a rubber material which can easily be formed to fit the dimension, contour and shape of first cavity 70 and second cavity 72 of front portion 48 of handle portion 32. To this end, first front insert 90 and second front insert 92 are tailored to the contour and shape of first cavity 70 and second cavity 72, respectively, to preferably ensure an interference fit. Such a fit is preferably facilitated by the gripping nature of the rubber material, which permits secured positioning of the first front insert and the second front insert into first and second cavities 70 and 72, respectively. Furthermore, such an interference fit eliminates the need for use of adhesives or other securing materials, which materials not only add to the cost of manufacturing bone marrow biopsy device 20, but also may constitute an unwanted element in a typically sterile, surgical environment. However, it is likewise contemplated that an adhesive or other securing material may be used with first and second front inserts 90 and 92 to enhance their secured placement in first and second cavities 70 and 72.

As is shown in FIG. 5, first front insert 90 and second front insert 92 further include peaks 91 and 93, respectively, while rear tactile insert member 58 includes peak 99. Preferably, peaks 91 and 93 correspond to peak 53 in first side portion 52, while peak 99 corresponds to peak 55 in second side portion 54 As will be described below, peaks not only provide a stop for handle cap 122 on inner rod 24, but also enhance the locking relationship of handle cap 122 onto handle portion 32 of outer cannula 22.

Preferably, and as is shown in FIG. 5, first front insert 90 and second front insert 92 extend out of first cavity 70 and second cavity 72 beyond outer peripheral ridge 74. This ensures that a user grips the portion of handle 32 which includes the tactile insert surface. Furthermore, as is shown in FIGS. 1–4, first front insert 90 and second front insert 92 preferably frame orientation indicia 78, to leave the indicia exposed to a user. However, it is certainly contemplated that front tactile insert member 56 may, like rear tactile insert 58, comprise a single piece extending over barrel 76 and orientation indicia 78, if the indicia is not desired and/or necessary.

Rear tactile insert member 58, shown in FIGS. 3, 5 and 6, comprises first wing 94, second wing 96 and connecting portion 98. Like front tactile insert member 56, rear tactile insert member 58 is preferably constructed from a rubber polymer material. However, it is likewise contemplated that rear tactile insert member 58 may be divided into two separate and distinct inserts, such as first front insert 90 and second front insert 92. Rear tactile insert member 58 is likewise preferably positioned and releasably secured in first cavity 80 and second cavity 82 of rear portion 50 by an interference fit, generated by the rubber-on-plastic contact of rear tactile insert member 58 with the cavity walls of rear portion 50.

Constructing front tactile insert member 56 and rear tactile insert member 58 from rubber also provides increased cushioning for a physician during use of bone marrow biopsy device 20. In particular, the rubber material gives upon compression by a physician's fingers. Inasmuch as handle portion 32 is often clenched with a strong, tightened grip as the bone marrow biopsy device is forced into a patient's bone, clenching places a large amount of stress on a physician's hand. Allowing a portion of that stress to be dissipated through the cushioning rubber eases the tension and stress placed on a physician's hand. Moreover, the rubber construction likewise provides a non-slip, gripping surface for a physician. This is especially useful as stringent clenching of handle portion 24 may lead to perspiration in a physician's palm. Additionally, there may be potential moisture in the surgical environment. As is well known, rubber acts as an excellent gripping surface in wet conditions.

The same non-slip characteristic of rubber also prevents inadvertent sliding or displacement of bone marrow biopsy device 20 from a table or other resting surface. In particular, in a resting state bone marrow biopsy device 20 lies at least partially on either front portion 48 or rear portion 50. Inasmuch as front tactile insert member 56 and/or rear tactile insert member 58 preferably extend outwardly beyond front peripheral ridge 74 and/or rear peripheral edge 84, one of the insert members comes into contact with a resting surface. Thus, the gripping nature of the insert members prevent inadvertent slippage or displacement of the bone marrow biopsy device from the resting surface.

Aside from functioning to enhance the gripping surface of handle portion 32 of bone marrow biopsy device 20, front tactile insert member 56 and rear tactile insert member 58 also provide additional weight to handle portion 32. As is known in the art, many physicians prefer a weighted handle for purposes of feel and balance. The particular orientation and positioning of first front insert 90, second front insert 92 and rear tactile insert member 58 ensures that such a weight distribution is substantially uniform throughout handle portion 32, so as to maintain a consistent weighted feel of bone marrow biopsy device 20 during use. To this end, insert members 56 and 58 are preferably solid materials, such as rubber, which add density to handle portion 32. It is contemplated that the insert members may have a density substantially equal to or greater than that of the remainder of handle portion 32.

Additionally, it is likewise contemplated that front tactile insert member 56 and rear tactile insert member 58 may likewise be constructed from alternative materials, such as other plastics, polymers or even metals, to provide increased weight to handle portion 32. Of course, it is further contemplated that insert members 56 and 58 may be constructed from a combination of two materials to provide both weight and a tactile gripping surface. It is even further contemplated that two separate insert members may be used in association with each cavity, one insert member in the bottom of the cavity to provide weight, and a second insert member near the top portion of the cavities to provide a tactile gripping surface, or other combinations as would be known by those of ordinary skill in the art with the present disclosure before them.

The use of insert members, instead of a solid handle portion, provides even further advantages in the manufacturing of bone marrow biopsy device 20. In particular, those of ordinary skill in the art with the present disclosure before them will readily appreciate that the molding process favors those molds having a substantially constant wall thickness with various transitions. The constant wall thickness is preferably somewhat thinner than that typically required to form the entirety of a typical handle portion of a bone marrow biopsy needle. Indeed, the process of molding an overly thick, non-uniform handle portion may lead to shrinking, contortion and/or deformation of the handle portion. Accordingly, the use of one or more insert members allows handle portion 32 to be molded in a desirable, cost effective, efficient manner having a substantially constant wall thickness with suitable transitions, while at the same time providing the valuable additional weight desired by many physicians.

Of course, tactile insert members 56 and 58 are not necessarily limited to placement solely within cavities in front portion 48 and rear portion 50. As is shown in FIG. 7, bone marrow biopsy device 20' includes single tactile insert 100 having a rear portion, first front portion 104, second front portion 106, first underside connecting portion 108 and second underside connecting portion 110. First underside connecting portion 108 and second underside connecting portion 110 provide a tactile gripping surface in the finger groove in the bottom portion of handle portion 32'. Thus, an improved gripping surface, and its cushioning benefits, is provided in an area of handle portion 32' which may receive at least as much clenching force from a physician's hand— leading to further increased grip, prevention of slippage and increased cushioning. Notably, first underside connecting portion 108 and second underside connecting portion 110 may be positioned directly over the bottom portion of handle portion 32'. However, and as is shown in FIG. 7, it is likewise contemplated that the outer peripheral ridges of the handle portion 32' may likewise include notches or paths specifically designed to accept first and second underside connecting portion 108 and 110. Furthermore, while shown as a single piece, tactile insert 100 may likewise comprise multiple insert member segments, as would be known by those in the art with the present disclosure before them.

In yet another embodiment, shown in FIG. 8, bone marrow biopsy device 20″ includes a tactile overlay. In particular, solid handle portion 112 is shown without any cavities, but instead with front and rear handle surfaces 115 and 117, respectively, which receive first tactile overlay 114 and second tactile overlay 116. First and second tactile overlays 114 and 116 are preferably adhered to the front and rear handle surfaces 115 and 117 of solid handle portion 112 to provide a tactile gripping surface and cushioning to facilitate use of the bone marrow biopsy device. Of course, while not shown, the tactile overlay may be extended to the bottom of solid handle portion 112, as well as to the sides and/or top thereof—in one or multiple pieces.

Inner rod 24 is shown in FIGS. 1, 2 and 4–6 as comprising cylindrical rod portion 120 and handle cap 122. Cylindrical rod portion 120 includes proximal end 124 and distal end 126, and as discussed above, may comprise any number of desirable hollow or solid rods.

Handle cap 122 comprises front 130, rear 132, top 134, locking member 136 and alignment member 138. Front 130 preferably includes alignment indicia 140, which act in combination with orientation indicia 78 on handle portion 32 to indicate proper orientation of inner rod 24 within outer cannula 22. In particular, a user knows when handle cap 122 is being positioned over handle portion 32 in a proper orientation when alignment indicia 140 corresponds to orientation indicia 78. Top 134 is shown in the drawings as having a substantially curved shape.

This shape is desirable as it contours to the shape of a user's palm, which directly contacts top 134 during use of bone marrow biopsy device 20. However, it is likewise contemplated that the handle cap 122 in general, and top 134 more particularly, may comprise any shape as would be known by those of ordinary skill in the art with the present disclosure before them. Additionally, while not shown in the drawings, handle cap 122 may further include a tactile member, such as a tactile overlay, to enhance gripping and/or cushioning thereof. It is contemplated that such tactile member may be positioned on top 134, front 130 and/or rear 132 of handle cap 122.

Locking member 136 is shown in FIG. 1 as comprising gripping prongs 142 and 144. Gripping prongs 142 and 144 preferably engage ridge 59 on connecting tube 42 on handle portion 32. Locking member 136 ensures that handle cap 122 is secured to handle portion 32, to facilitate simultaneous insertion of outer cannula is 22 and inner rod 24 into a patient.

Additionally, the secured locking relationship of handle cap 122 onto handle portion 32 of outer cannula 22 is enhanced by front tactile insert member 56 and rear tactile insert member 58. In particular, inasmuch as the insert members preferably extend beyond front peripheral outer ridge 74 and rear outer peripheral ridge 84, the inside of handle cap 122 preferably contacts a portion of insert member 56 and 58. Specifically, peaks 91 and 93 in front insert member 56 and peak 99 in rear insert member 58 are abutted by the inside surface of handle cap 122 to create an interference fit of handle cap 122 onto handle portion 32. This interference fit enhances the locking and secured relationship between handle cap 122 and handle portion 32, to facilitate simultaneous use of inner rod 24 and outer cannula 22.

Alignment member 138 is shown in FIG. 1 as comprising a shoulder. Alignment member 138 preferably fits into notch 60 in top portion 44 of handle portion 32, but only if handle cap 122 is oriented over handle portion 32 in a manner in which alignment indicia 140 aligns with orientation indicia 78. In particular, alignment member 138 fits only into the wider portion of notch 60, thus precluding secured attachment of handle cap 122 onto handle portion 32 in an orientation where there is no alignment of the handle cap with the handle portion of the outer cannula. Thus, a physician is precluded from attaching inner rod 24 to outer cannula 22 improperly. Of course, while alignment member 138 is shown as a shoulder, such an aligning function may be performed in a number of ways as would be known by those of ordinary skill in the art with the present disclosure before them.

Bone marrow biopsy device 200 is shown in FIGS. 9–19 as comprising outer cannula 202, outer cannula handle 204, inner rod 206, inner rod handle 208, and locking element 300. While inner rod 206 is shown in the drawings as comprising a sharpened stylet or obturator used for cutting through soft and hard bone tissue, inner rod 206 may likewise comprise a hollow inner cannula used for sampling bone marrow tissue, an ejector rod for forcing that tissue from that outer cannula, as well as other types of inner rods well known by those of ordinary skill in the art with the present disclosure before them.

Outer cannula 202, shown in FIGS. 9 and 10, includes cylindrical tube 210. Cylindrical tube 210 includes both proximal end 214 and distal end 216. Distal end 216 is shown in FIG. 9 as having saddle point configuration 217 with sharp edges. Such a configuration, as is well known in the art, facilitates cutting through both soft and hard tissue, thus facilitating the entry of the bone marrow biopsy device into a bone marrow sampling region. However, it is likewise contemplated that other distal end point configurations may likewise be utilized with the present invention, depending on the specific biopsy application. Moreover, distal end 216 of cylindrical tube 210 may likewise include an inner tapered portion to facilitate bone marrow retrieval, such as disclosed in Mittermeier, U.S. Pat. No. 6,063,037.

Outer cannula handle 204 is shown in FIGS. 9–13 as including a front portion 218, a rear portion 220, a top portion 222, a bottom portion 224, a first side portion 226, a second side portion 228, an aperture 230, a connecting tube 232, a notch 234, and a locking member 304. Aperture 230 connects cylindrical tube 210 of outer cannula 202 with connecting tube 232. Locking member 304 comprises flange element 340 to facilitate locking of inner rod handle 208 to outer cannula handle 204, as will be described in more detail below. As shown in FIG. 14, flange element 340 is situated on the outer surface of connecting tube 232 and forms part of the structure of connecting tube 232. However, it is also contemplated that the flange element could instead be situated on the inner surface of connecting tube 232, or additionally could constitute an independent structural element not associated with connecting tube 232.

Figure 17:
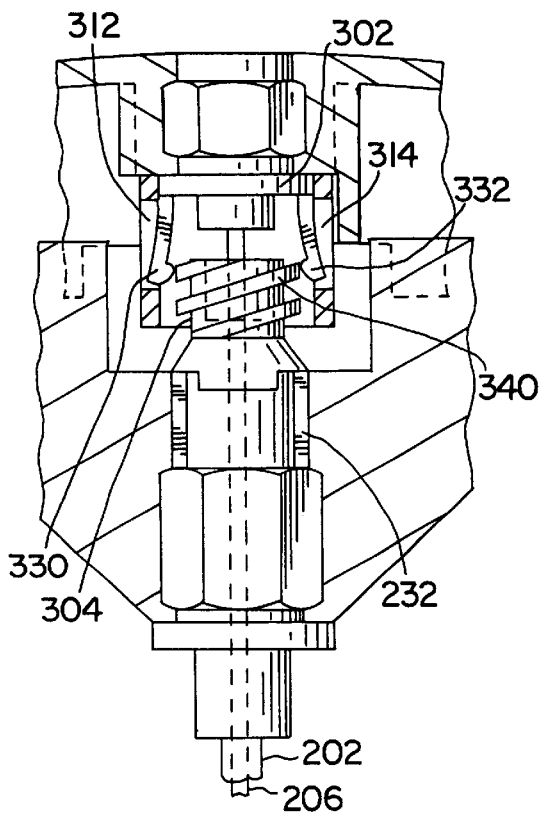
FIG. 17 is a cross-sectional view of the locking element of the bone marrow biopsy device shown in FIG. 9 in its unlocked orientation, showing the prongs of the inner rod handle locking member being withdrawn over the flange element of the outer cannula handle locking member, during separation of the outer cannula handle and inner rod handle.

Flange element 340 may comprise a threaded region 342, such as that shown in FIGS. 14, 15, and 17, or any other contoured portion which facilitates receipt of inner rod 206. Threaded region 342 serves an additional purpose beyond merely comprising locking member 304—as it also conventionally permits the user to attach external devices such as a suction device or a miniature endoscope for examining the desired region of the body, without having to insert a separate needle into the patient. Upon removal of inner rod 206 from outer cannula 202, to the user can connect a desired external device to outer cannula 202 by means of threaded region 342 without having to remove or disturb the placement of outer cannula 202. Thus, outer cannula 202 can be used not only for the removal of tissue from the patient but also for various other uses such as described above. Likewise, threaded region 342 simultaneously serves as an attachment flange, or locking member, for locking element 300.

Top portion 222 includes notch 234 and sloping portions 236 and 238. Notch 234, best seen in FIGS. 11 and 12, permits connecting tube 232 to exit aperture 230 of outer cannula handle 204. As can be seen from the drawings, notch 234 is preferably off-center relative to connecting tube 232, so as to provide a larger opening on one side of connecting tube 232. Sloping portions 236 and 238 preferably extend from top portion 222 down to side portions 226 and 228, and facilitate a contoured fit of inner rod handle 208 onto outer cannula handle 204.

Bottom portion 224 preferably includes recesses 240 and 242, best seen in FIGS. 11 and 12. The recesses facilitate grasping of outer cannula handle 204 by a user. However, while recesses 240 and 242 are certainly preferred, outer cannula handle 204 may likewise be rounded or squared on bottom portion 224 without any finger grooves or special receptacles for a user's fingers.

Front portion 218, shown in FIG. 11, includes first cavity 270, second cavity 272, peripheral ridge 274, and barrel portion 276. First cavity 270 and second cavity 272, as shown in FIG. 9, are positioned on either side of barrel portion 276, which further includes orientation indicia 278. As can be seen in FIGS. 11 and 12, orientation indicia 278 helps a user distinguish between the front and rear sides of bone marrow biopsy device 200, so as to properly indicate the orientation of distal end 216 of cylindrical tube 210 of outer cannula 202 and/or the orientation of cylindrical rod 250 of inner rod 206, for instance in those applications where the inner rod comprises a sharpened stylet. Moreover, while orientation indicia 278 is shown in the drawings as comprising a stepped arrow, any orientation indicia may be used in conjunction with the present invention as would be known by those with ordinary skill in the art with the present disclosure before them. Peripheral ridge 274 forms a wall around first cavity 270 and second cavity 272.

In one embodiment of the invention, front portion 218 also includes front grip enhancement member 290, as shown in FIGS. 9 and 10. Front grip enhancement member 290 preferably comprises rubber or a similar resilient material which can easily be formed to fit the dimension, contour and shape of first cavity 270 and second cavity 272 of front portion 218. Furthermore, front grip enhancement member 290 is shaped so as not to cover orientation indicia 278. Front grip enhancement member 290 is preferably tailored to the contour and shape of first cavity 270 and second cavity 272, respectively, to preferably ensure an interference fit. Such a fit is facilitated by the gripping nature of the rubber material, which permits secured positioning of front grip enhancement member 290 into first and second cavities 270 and 272, respectively. Furthermore, such an interference fit eliminates the need for the use of adhesives or other securing materials, which materials not only add to the cost of manufacturing bone marrow biopsy device 200, but also may constitute an unwanted element in a typically sterile, surgical environment. However, it is likewise contemplated that an adhesive or other securing material may be used with front grip enhancement member 290 to enhance its secured placement in first and second cavities 270 and 272.

Rear portion 220, shown in FIG. 12, likewise includes first cavity 280, second cavity 282, peripheral ridge 284, and barrel portion 286. Like first cavity 270 and second cavity 272 on front portion 218, first cavity 280 and second cavity 282 are separated by barrel portion 286 and enclosed by peripheral ridge 284. In addition, rear portion 220 may include a rear grip enhancement member (not shown) similar in all particulars to front grip enhancement member 290. Because of the absence of an orientation indicia on rear portion 220, the rear grip enhancement member comprises a single piece extending over barrel portion 286. However, if desired, an indicia may be placed on barrel portion 286 corresponding to orientation indicia 278 on front portion 218, in which case the rear grip enhancement member would be shaped so as not to cover said indicia.

Preferably, and as is shown in FIGS. 9 and 10, front grip enhancement member 290 extends out of first and second cavities 270 and 272 beyond peripheral ridge 274. Similarly, a rear grip enhancement member, if present, would extend out of first and second cavities 280 and 282 beyond peripheral ridge 284. This ensures that a user grips the portion of bone marrow biopsy device 200 which includes the grip enhancing surfaces. Furthermore, as is shown in FIGS. 9–11, front grip enhancement member 290 preferably frames orientation indicia 278, to leave the indicia visible to the user. However, it is certainly contemplated that front grip enhancement member 290 may comprise a single piece extending over barrel portion 276 and orientation indicia 278, if the indicia is not desired.

Inner rod 206 is shown in FIGS. 9 and 10 as comprising cylindrical rod 250. Cylindrical rod 250 includes proximal end 254 and distal end 256 and, as discussed above, may comprise any number of desirable hollow or solid rods.

Inner rod handle 208 comprises front portion 258, rear portion 260, top portion 262, notch 263, alignment member 264, and locking member 302 (as shown in FIG. 14). Notch 263 preferably corresponds with notch 234 on outer cannula handle 204 in order to provide an aperture for the user to manipulate locking element 300, as described below. Alignment member 264 fits into the larger side of notch 234 on outer cannula handle 204 when outer cannula handle 204 and inner rod handle 208 are joined together. However, alignment member 264 is positioned such that it will fit into notch 234 only if outer cannula handle 204 and inner rod handle 208 are brought together in the proper orientation. If the user attempts to join outer cannula handle 204 and inner rod handle 208 improperly, i.e., if the handles are turned one-hundred eighty degrees from their proper orientation, alignment member 264 will not fit into notch 234 because of the fact that notch 234 is offset with respect to connecting tube 232, as seen in FIGS. 11 and 12.

Further, front portion 258 of inner rod handle 208 preferably includes alignment indicia 265, which acts in combination with orientation indicia 278 on outer cannula handle 204 to indicate proper orientation of outer cannula handle 204 and inner rod handle 208. Specifically, a user knows when inner rod handle 208 is being positioned over outer cannula handle 204 properly when alignment indicia 265 on inner rod handle 208 corresponds to orientation indicia 278 on outer cannula handle 204.

Top portion 262 of inner rod handle 208 is shown in the drawings as having a substantially curved shape. This shape is desirable as it contours to the shape of a user's palm, which directly contacts top portion 262 during use of bone marrow biopsy device 200. However, it is likewise contemplated that the inner rod handle 208 in general, and top portion 262 more particularly, may comprise any shape as would be known by those of ordinary skill in the art, with the present disclosure before them.

Figure 16:
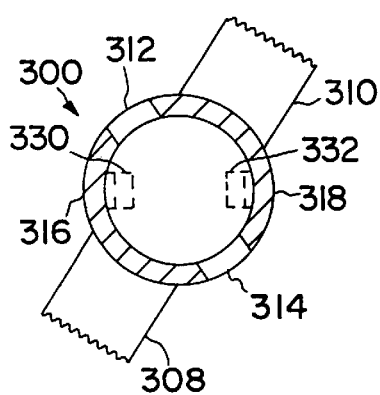
FIG. 16 is a cross-sectional view of the locking element and the prongs of the inner rod handle locking member of the bone marrow biopsy device shown in FIG. 15, showing the orientation of the prongs relative to the slots in the locking element, when the locking element is in its locked orientation.
Figure 18:
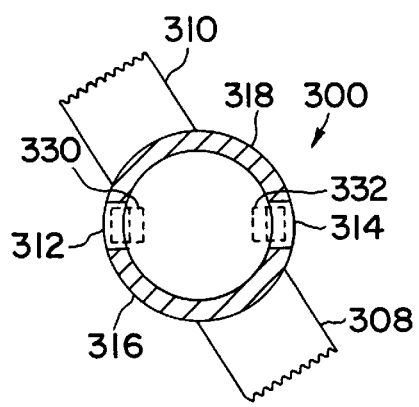
FIG. 18 is a cross-sectional view of the locking element and the prongs of the inner rod handle locking member of the bone marrow biopsy device shown in FIG. 17, showing the orientation of the prongs relative to the slots in the locking element, when the locking element is in its unlocked orientation.

Locking member 302 of inner rod handle 208 comprises prongs 330 and 332, as shown in FIG. 14. Prongs 330 and 332 are situated opposite one another as shown in FIGS. 16 and 18. Prongs 330 and 332 are flexible and capable of bending outward during joinder and separation of outer cannula handle 204 and inner rod handle 208 to engage and pass over the flange element 340, as described in detail below. However, it is likewise contemplated that prongs 330 and 332 could instead bend inward during joinder and separation of outer cannula handle 204 and inner cannula handle 208 to engage a flange element located on the inner surface of connecting tube 232, as described above.

Locking element 300 is shown in FIG. 14 as comprising cylindrical sleeve 306, front locking tab 308, and rear locking tab 310. Cylindrical sleeve 306 further comprises slots 312 and 314, sidewalls 316 and 318, and top portion 320. Slots 312 and 314 are positioned opposite one another, as shown in FIGS. 16 and 18.

Cylindrical sleeve 306 is attached to inner rod handle 208, as shown in FIGS. 11 and 12, in such a manner that it surrounds prongs 330 and and may be freely rotated about prongs 330 and 332 by manipulating front locking tab 308 and/or rear locking tab 310. When prongs 330 and 332 are aligned with slots 312 and 314, prongs 330 and 332 are able to bend outward so that they partially protrude through slots 312 and 314, as shown in FIG. 17. This corresponds to the unlocked orientation of locking element 300.

In order for a user of bone marrow biopsy device 200 to join outer cannula handle 204 and inner rod handle 208 together, locking element 300 must be in its unlocked orientation. When the user inserts inner rod 206 into outer cannula 202, prongs 330 and 332 encounter flange element 340 on connecting tube 242, as shown in FIG. 17. In order for prongs 330 and 332 to pass over flange element 340, prongs 330 and 332 must bend outward, partially protruding through slots 312 and 314, as shown in FIGS. 17 and 18. If locking element 300 is not in its unlocked orientation at this point, then prongs 330 and 332 are constrained by sidewalls 316 and 318 of cylindrical sleeve 306 and cannot bend outward to fit over flange element 340. Therefore, the user must check to ensure that locking element 300 is in its unlocked orientation before attempting to join outer cannula handle 204 and inner rod handle 208.

Once prongs 330 and 332 have passed over flange element 340, outer cannula handle 204 and inner rod handle 208 are joined together, albeit not securely. As long as locking element 300 remains in its unlocked orientation, outer cannula handle 204 and inner rod handle 208 can be easily separated by merely pulling them apart.

In order to ensure that outer cannula handle 204 and inner rod handle 208 are securably locked together to prevent their accidental separation during use, locking element 300 must be placed in its locked orientation. The user may place locking element 300 into its locked orientation by manipulating front locking tab 308 and/or rear locking tab 310 to rotate locking element 300 about prongs 330 and 332. Once locking element 300 has been rotated such that prongs 330 and 332 are offset from slots 312 and 314, locking element 300 is then in its locked orientation, as shown in FIGS. 15 and 16. In this orientation, prongs 330 and 332 are confined by sidewalls 316 and 318 of cylindrical sleeve 306 so that they cannot protrude through slots 312 and 314. As a result, prongs 330 and 332 may not be disengaged from flange element 340 without using destructive force.

Therefore, outer cannula handle 204 and inner rod handle 208 cannot be separated by the user without returning locking element 300 to its unlocked orientation. This will serve to prevent accidental and undesirable separation of outer cannula handle 204 and inner rod handle 208 during use.

Similarly, when the user desires to separate outer cannula handle 204 and inner rod handle 208 in order to remove inner rod 206 from outer cannula 202, he/she must engage front locking tab 308 and/or rear locking tab 310 in order to rotate locking element 300 with respect to prongs 330 and 332, thereby returning locking element 300 to its unlocked orientation. When locking element 300 is once again in its unlocked orientation, the user may easily separate outer cannula handle 204 and inner rod handle 208 by pulling on inner rod handle 208.

Locking element 300 works in association with front locked indicia 266, front unlocked indicia 267, rear locked indicia 268, and rear unlocked indicia 269, which are located on front portion 258 and rear portion 260 of inner rod handle 208, respectively, to indicate to the user whether locking element 300 is in its locked or unlocked orientation. Specifically, front locked indicia 266 and front unlocked indicia 267 consist of the words "lock" and "unlock", respectively, or similar language, printed on opposite sides of notch 263 on front portion 258 of inner rod handle 208, as shown in FIG. 11. Likewise, rear locked indicia 268 and rear unlocked indicia 269 consist of the words "lock" and "unlock", respectively, or similar language, printed on opposite sides of notch 263 on rear portion 260 of inner rod handle 208, as shown in FIG. 12. When front and rear locking tabs 308 and 310 are positioned on the side of notch 263 corresponding to front and rear unlocked indicia 267 and 269, as seen in FIGS. 11 and 12, this indicates to the user that locking element 300 is in its unlocked orientation. Similarly, when front and rear locking tabs 308 and 310 are positioned on the side of notch 263 corresponding to front and rear locked indicia 266 and 268, respectively, this indicates to the user that locking element 300 is in its locked orientation.

In another embodiment of bone marrow biopsy device 200, inner rod handle 208 may further include a front grip enhancement member 294 and a rear grip enhancement member 296, as shown in FIG. 19, to enhance gripping of bone marrow biopsy device 200 and to prevent the palm of the user from coming into contact with front locking tab 308 and rear locking tab 310 during use. This would prevent the user from accidentally causing locking element 300 to be changed from its locked orientation to its unlocked orientation by engaging front locking tab 308 and/or rear locking tab 310 with the palm of his hand during use. This will serve to prevent the unintended and undesired separation of outer cannula handle 204 and inner rod handle 208 while outer cannula 202 and inner rod 206 are inside a patient.

Another embodiment of the invention, bone marrow biopsy device 200', is shown in FIGS. 20–23 as including outer cannula handle 350, inner rod handle 352, locking element 354, outer cannula 356 and inner rod 358. Outer cannula handle 350 further includes locking member 360 and orientation indicia 364, and is otherwise substantially similar to outer cannula handle 204 in the previous embodiment of FIGS. 9 through 19. Likewise, inner rod handle 352 further includes locking member 370, recess 376, slot 378 and alignment indicia 382, and is otherwise substantially similar to inner rod handle 208 in that same embodiment.

Figure 21:
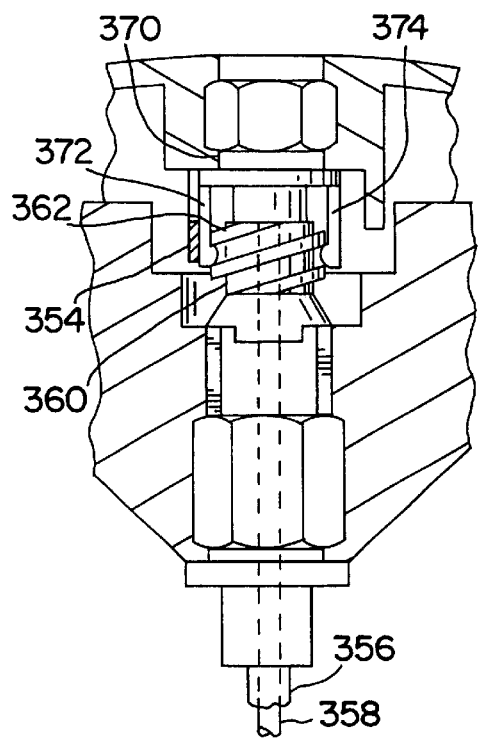
FIG. 21 is a cross-sectional view of the locking element of the bone marrow biopsy device shown in FIG. 20, in its locked orientation, showing at least one of the prongs of the inner rod handle locking member engaged with the flange element of the outer cannula handle locking member, as confined by the locking element.
Figure 22:
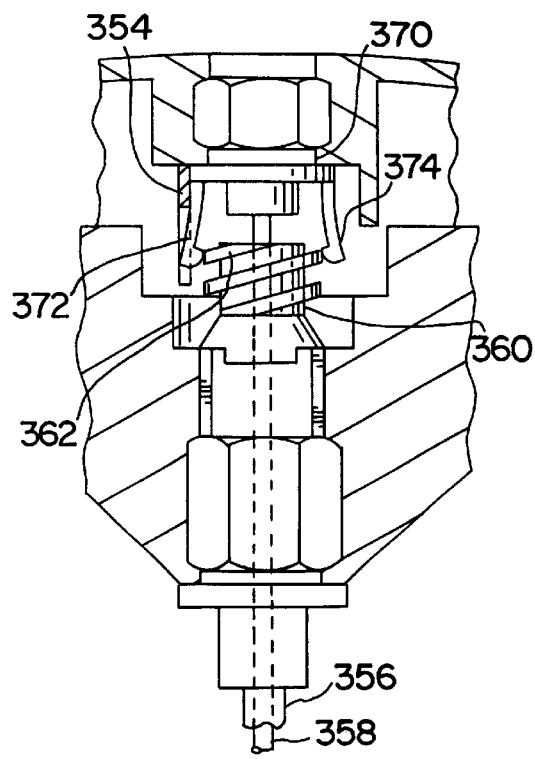
FIG. 22 is a cross-sectional view of the locking element of the bone marrow biopsy device shown in FIG. 20, in its unlocked orientation, showing the prongs of the inner rod handle locking member being withdrawn from engagement with the flange element of the outer cannula handle locking member, during separation of the outer cannula handle and inner rod handle.

Locking member 360 of outer cannula handle 350 is shown in FIGS. 21 and 22 as including flange element 362, similar to flange element 340 in the previous embodiment.

Flange element 362 is also shown comprising a conventional thread for attachment of suction or other devices to outer cannula handle 350. Similarly, locking member 370 of inner rod handle 352 includes prongs 372 and 374, as in the previous embodiment.

Figure 20:
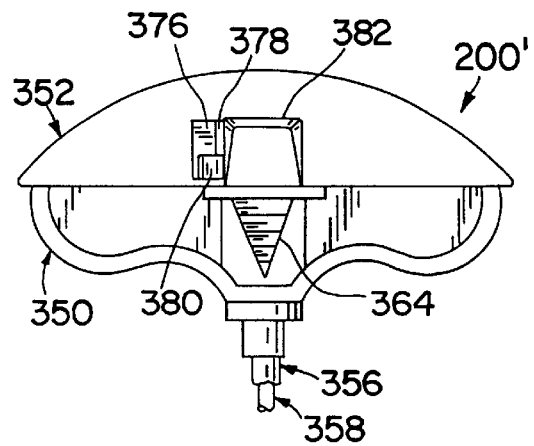
FIG. 20 is a front elevational view of the bone marrow biopsy device according to another embodiment of the present invention showing the outer cannula handle and inner rod handle joined together and the locking element in its locked orientation.
Figure 23:
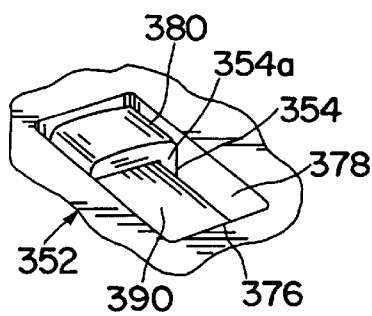
FIG. 23 is a perspective view of the finger tab portion of the locking element of the bone marrow biopsy device shown in FIG. 20, showing the positioning of the finger tab in the recess located on the front of the inner cannula handle in its unlocked position.

Locking element 354 comprises a thin u-shaped bar positioned within slot 378 in inner rod handle 352, the end of which bar is bent inward to form finger tab 380, which reciprocates along ridge 390, as shown in FIGS. 20 and 23. Locking element 354 is constrained to move up and down in slot 378, and has two positions (lower, shown in FIGS. 20 and 21, and upper, shown in FIGS. 22 and 23) which correspond to the unlocked and locked orientations of locking element 354, respectively. Locking element 354 also includes a corresponding finger tab on the rear portion of inner cannula handle 352 (not shown). Finger tab 380 is set in recess 376 on inner rod handle 352 in order to prevent inadvertent manipulation of locking element 354 by the user of the device. Finger tab 380 can be moved up and down to place locking element 354 in its locked and unlocked orientation, as described below. In its locked orientation, the lower stem portion 354a of locking element 354 is maintained in place by the frictional engagement between locking member 370 and ridge 390.

Locking element 354 is in its unlocked orientation when locking element 354 is in the top position, as shown in FIG. 22. When the user desires to join outer cannula handle 350 and inner rod handle 352 together, he/she slides locking element 354 to its top position by pushing finger tab 380 up. In this position, prongs 372 and 374 are unconstrained and are therefore able to bend outward to pass over flange element 362, as shown in FIG. 22. Once prongs 372 and 374 have passed over flange element 362, the user then slides locking element 354 to its bottom position to place locking element 354 in its locked orientation. Once locking element 354 has been placed in its bottom position, gravity and friction work to prevent it from returning to the top position, thereby preventing locking device 354 from returning to its unlocked orientation absent intentional manipulation by the user.

In the locked orientation, prong 372 is held in place by locking element 354, as shown in FIG. 21. As a result, prong 372 is not allowed to bend outwardly to pass over flange element 362, thereby preventing removal of inner rod handle 352 from outer cannula handle 350. Thus, locking element 354 works in a similar fashion to locking element 300, in the previous embodiment, to allow the user to lock and unlock outer cannula handle 350 and inner rod handle 352—without affecting the orientation of the handles relative to one another. While, in this embodiment, locking element 354 only constrains prong 372, it is certainly contemplated that locking element 354 can encompass an additional portion on the opposite side of locking member 370 of inner rod handle 352, which would likewise serve to simultaneously constrain prong 374 as well. In such an embodiment, finger tab 380 could be extended across the center portion of inner cannula handle 352 to connect the two portions of the locking element.

The foregoing description and drawings are merely to explain and illustrate the inventions, and the inventions are not limited thereto except insofar as the independent claims are so limited, as those skilled in the art with the present disclosure before them will be able to make modifications and variations therein without departing from the scope of the invention.

What is claimed is:

1. A bone marrow biopsy device for accessing and withdrawing samples of bone marrow tissue from a living patient, said bone marrow biopsy device having a locking handle for integrating the individual handle portions of said bone marrow biopsy device without risking the inadvertent release thereof, said bone marrow biopsy device comprising:

an outer cannula having a proximal end, a distal end, and a substantially hollow cross-section between said proximal and distal ends;

an outer cannula handle having a locking member, said outer cannula handle operably attached to said outer cannula at said proximal end of said outer cannula;

an inner rod capable of being telescopically inserted into and retracted from said outer cannula, said inner rod having a proximal end and a distal end;

an inner rod handle having a locking member, said inner rod handle operably attached to said inner rod at said proximal end of said inner rod, said inner rod handle and said outer cannula handle being capable of forming an integrated, aligned handle assembly for simultaneously aligning the orientation of the distal ends of the outer cannula and inner rod; and a locking element associated with said locking members on each of said outer cannula handle and said inner rod handle; and said locking element being capable of alternatively locking and releasing said outer cannula handle and said inner rod handle in said aligned orientation without having to reorient the position of either of said outer cannula handle and said inner rod handle.

2. The bone marrow biopsy device according to claim 1 wherein said inner rod handle fits completely over said outer cannula handle such that said outer cannula handle nests within said inner rod handle when said outer cannula handle and said inner rod handle are joined together.

3. The bone marrow biopsy device according to claim 1 wherein said locking member associated with said outer cannula handle comprises at least one flange element located on said outer cannula handle.

4. The bone marrow biopsy device according to claim 3 wherein said locking member associated with said inner rod handle comprises at least one prong, said at least one prong capable of engaging with said at least one flange element to prevent disengagement of said outer cannula handle and said inner rod handle from one another.

5. The bone marrow biopsy device according to claim 4 wherein said locking element comprises a cylindrical sleeve surrounding said at least one prong and said at least one flange element, said cylindrical sleeve preventing disengagement of said at least one prong from said at least one flange element when said locking element is in a locked orientation.

6. The bone marrow biopsy device according to claim 3 wherein said at least one flange element further comprises at least a portion of a thread as conventionally found on connections for medical devices, said thread allowing the user to attach a threaded component to said outer cannula handle after removing said inner rod from said outer cannula.

7. The bone marrow biopsy device according to claim 5 wherein said cylindrical sleeve includes at least one slot such that said at least one prong is allowed to partially protrude through said at least one slot when said locking element is in an unlocked orientation in order to allow disengagement of said outer cannula handle from said inner rod handle.

8. The bone marrow biopsy device according to claim 7 wherein said locking element may be rotated with respect to said at least one prong and said at least one flange element in order to place said locking element in a locked orientation wherein said at least one prong is prevented from protruding through said at least one slot, thereby preventing said outer cannula handle and said inner rod handle from becoming disengaged.

9. The bone marrow biopsy device according to claim 8 further including at is least one locking tab associated with said cylindrical sleeve, said at least one locking tab facilitating rotation of said locking element with respect to said at least one prong and said at least one flange element, thereby permitting locking and unlocking of said locking element without affecting the orientation of said handles themselves.

10. The bone marrow biopsy device according to claim 1 in which the invention further includes an alignment member associated with at least one of said outer cannula handle and said inner rod handle, said alignment member serving to ensure proper orientation of said outer cannula handle and said inner rod handle during engagement of said handles with one another, thereby preventing the user from aligning said handles improperly.

11. The bone marrow biopsy device according to claim 10 wherein at least one of said outer cannula handle and said inner rod handle further includes an opening capable of receiving said alignment member, said opening positioned such that said outer cannula handle and said inner rod handle can only be fully and properly joined when they are properly oriented with respect to one another, thereby preventing the user from aligning said handles improperly.

12. The bone marrow biopsy device according to claim 11 further including an alignment indicia for visually indicating the proper orientation of said outer cannula handle and said inner rod handle with respect to one another during engagement of said handles.

13. The bone marrow biopsy device according to claim 1 in which the invention further includes a locking indicia for indicating whether said locking element is in a locked or unlocked orientation when said outer cannula handle and said inner rod handle are engaged with one another.

14. The bone marrow biopsy device according to claim 9 wherein the invention further includes a locking indicia comprising text printed on at least one of said outer cannula handle and said inner rod handle, said text corresponding with the position of said at least one locking tab to indicate to the user whether said locking element is in a locked or unlocked orientation.

15. The bone marrow biopsy device according to claim 1 in which the invention further includes at least one grip enhancement member associated with at least one of said outer cannula handle and said inner rod handle, said at least one grip enhancement member facilitating handling and use of said bone marrow biopsy device.

16. The bone marrow biopsy device according to claim 15 wherein said at least one grip enhancement member is formed from a material distinct from said outer cannula handle and said inner rod handle.

17. The bone marrow biopsy device according to claim 16 wherein said at least one grip enhancement member is at least partially constructed from rubber.

18. The bone marrow biopsy device according to claim 15 wherein said at least one grip enhancement member extends outwardly beyond the end of said at least one locking tab, thereby preventing the palm of the user from coming into inadvertent operable contact with and possibly engaging said locking element during use of said bone marrow biopsy device.

19. The bone marrow biopsy device according to claim 15 wherein at least a portion of said at least one grip enhancement member extends outwardly beyond at least a portion of said outer cannula handle to enhance the secured engagement of said outer cannula handle with said inner rod handle by forming an interference fit between said inner rod handle and said at least one grip enhancement member.

20. The bone marrow biopsy device according to claim 4 wherein said locking element comprises at least one bar extending at least partially through said inner rod handle, said at least one bar preventing disengagement of said at least one prong from said at least one flange element when said locking element is in its locked orientation.

21. The bone marrow biopsy device according to claim 20 wherein said locking element further includes at least one finger tab to facilitate manipulation of said locking element by the user.

22. The bone marrow biopsy device according to claim 1 wherein said inner rod comprises at least one of an inner cannula, a stylet, an obturator, and an ejector rod.

\* \* \* \* \*

UNITED STATES PATENT AND TRADEMARK OFFICE
CERTIFICATE OF CORRECTION

PATENT NO.     : 6,312,394 B1
DATED          : November 6, 2001
INVENTOR(S)    : Fleming, III It is certified that error appears in the above-identified patent and that said Letters Patent is hereby corrected as shown below:

Column 11,
Line 49, delete "is", after "cannula"

Column 12,
Line 65, after "202", delete "to"

Column 19,
Line 9, after "at", delete "is"

Signed and Sealed this

Third Day of December, 2002

JAMES E. ROGAN
*Director of the United States Patent and Trademark Office*